US011887351B1

(12) United States Patent
Ignat et al.

(10) Patent No.: US 11,887,351 B1
(45) Date of Patent: Jan. 30, 2024

(54) SYSTEM AND METHOD FOR HYPERSPECTRAL IMAGE-BASED QUALITY CONTROL ANALYSIS OF CROP LOADS

(71) Applicants: Timea Ignat, Midreshet Ben Gurion (IL); Guy Morgan, Tel Aviv (IL); Eliyahu Osherovich, Haifa (IL); Ze'ev Schmilovitch, Yehud-Monosson (IL)

(72) Inventors: Timea Ignat, Midreshet Ben Gurion (IL); Guy Morgan, Tel Aviv (IL); Eliyahu Osherovich, Haifa (IL); Ze'ev Schmilovitch, Yehud-Monosson (IL)

( * ) Notice: Subject to any disclaimer, the term of this patent is extended or adjusted under 35 U.S.C. 154(b) by 0 days.

(21) Appl. No.: 18/226,543

(22) Filed: Jul. 26, 2023

(51) Int. Cl.
*G06V 10/00* (2022.01)
*G06V 10/58* (2022.01)
(Continued)

(52) U.S. Cl.
CPC ............. *G06V 10/58* (2022.01); *G01N 33/02* (2013.01); *G06T 7/0004* (2013.01); *G06V 20/68* (2022.01);
(Continued)

(58) Field of Classification Search
CPC ........ G06V 10/58; G06V 20/68; G01N 33/02; G06T 7/0004; G06T 2207/10036; G06T 2207/20081; G06T 2207/30128
See application file for complete search history.

(56) References Cited

U.S. PATENT DOCUMENTS 6,888,082 B1 5/2005 Blanc
9,551,616 B2 1/2017 Mcquilkin et al.
(Continued)

FOREIGN PATENT DOCUMENTS

CA 2954625 A1 12/2015
CN 108372133 A 7/2018
(Continued)

OTHER PUBLICATIONS

Maftoonazad et al (2011) Artificial Neural Network Modeling of Hyperspectral Radiometric Data for Quality Changes Associated with Avocados During Storage, journal of Food Processing and Preservation, 35:432-446. https://doi.org/10.1111/j.1745-4549.2010.00485.x.

(Continued)

*Primary Examiner* — Ping Y Hsieh
(74) *Attorney, Agent, or Firm* — The Roy Gross Law Firm, LLC; Roy Gross

(57) ABSTRACT

System and method for imaging-based quality assessment of raw produce loads, including an imaging structure comprising a mounting beam, light sources; optical sensors, and additional sensors; wherein the mounting beam is configured to allow vertical, lateral and/or longitudinal and movement of the measurement chamber. The system also includes a processing unit configured to control the vertical, lateral and/or longitudinal movement of the measurement chamber relative to the mounting beam, control opto-mechanical parameters of the optical sensors, control the position, orientation, light projection and/or light intensity of the light sources; trigger signal acquisition, receiving and fusing spectral data from the optical sensors with data from the additional sensors; and feeding the fused data into machine learning algorithm and/or big-data analytics model, to derive internal and/or external quality attributes of the produce.

20 Claims, 7 Drawing Sheets

(51) Int. Cl.

| | |
|---|---|
| ***G06V 20/68*** | (2022.01) |
| ***G06T 7/00*** | (2017.01) |
| ***G01N 33/02*** | (2006.01) |

(52) U.S. Cl.

CPC ............... *G06T 2207/10036* (2013.01); *G06T 2207/20081* (2013.01); *G06T 2207/30128* (2013.01)

(56) References Cited

U.S. PATENT DOCUMENTS

| | | | |
|---|---|---|---|
| 10,222,260 | B2 | 3/2019 | Mcquilkin et al. |
| 10,255,670 | B1 * | 4/2019 | Wu ........................ H04N 7/183 |
| 10,288,594 | B2 | 5/2019 | Blanc |
| 10,395,503 | B2 | 8/2019 | Hummer |
| 10,408,748 | B2 | 9/2019 | Schwartzer et al. |
| 10,555,505 | B2 | 2/2020 | Hummer et al. |
| 10,655,015 | B2 | 5/2020 | Vardanyan et al. |
| 10,839,503 | B2 | 11/2020 | Schwartzer et al. |
| 10,902,581 | B2 | 1/2021 | Nipe et al. |
| 10,902,577 | B2 | 6/2021 | Nipe et al. |
| 11,422,030 | B2 | 8/2022 | Mcquilkin et al. |
| 11,443,417 | B2 | 9/2022 | Nipe et al. |
| 11,445,733 | B2 | 9/2022 | Holland et al. |
| 11,769,244 | B2 * | 9/2023 | McDonnell .......... G06V 10/141 382/110 |
| 2012/0321759 | A1 | 12/2012 | Marinkovich et al. |
| 2016/0368011 | A1 * | 12/2016 | Feldhaus ............... B05B 12/124 |
| 2019/0340749 | A1 | 7/2019 | Schwartzer et al. |
| 2020/0111342 | A1 | 4/2020 | Hummer et al. |
| 2022/0192076 | A1 * | 6/2022 | Sharma .................. A01B 76/00 |
| 2022/0252568 | A1 | 8/2022 | Schwartzer et al. |
| 2022/0299493 | A1 | 9/2022 | Pattison et al. |
| 2022/0327685 | A1 | 10/2022 | Rogers et al. |
| 2023/0133152 | A1 * | 5/2023 | Barnehama ............... G06T 7/90 382/141 |

FOREIGN PATENT DOCUMENTS

| | | | |
|---|---|---|---|
| CN | 109279266 | A | 1/2019 |
| CN | 112974303 | A | 6/2021 |
| CN | 11329066 | | 8/2021 |
| CN | 113418874 | A | 9/2021 |
| KR | 20070026501 | A | 3/2007 |
| WO | 2005108956 | A1 | 11/2005 |
| WO | 2007041755 | A1 | 4/2007 |

OTHER PUBLICATIONS

Mishra et al (2021) Assesssing avocado firmness with different dehydration levels in a multi-sensor framework, Infrared Physics and Technology, 118. https://doi.org/10.1016/j.infrared.2021.103901.

* cited by examiner

SYSTEM AND METHOD FOR HYPERSPECTRAL IMAGE-BASED QUALITY CONTROL ANALYSIS OF CROP LOADS

TECHNOLOGICAL FIELD

The present disclosure generally relates to a system and method for hyperspectral imaging-based quality assessment of crop loads.

BACKGROUND

Acceptance checkup/test of produce are conducted as routine procedures for fruits and vegetables in the gate/entrance of warehouses, packinghouses, storages, canneries, wineries etc. Sometimes the quality evaluation as well as the weight of the transport is a "go not go" regulation procedure, in other cases it is the base for payment calculation. Typically, the evaluation involves a sampling of produce followed by shipment of the samples to an associated laboratory facility for testing e.g. of sugar, starch, and acidity contents and of internal disorders, which in turn is laborious and time consuming thus delaying and detain the acceptance of a transport.

Recently, imaging has been applied as an emerging scientific tool in nondestructive fruit and vegetable quality assessment. However, these imaging methods have not yet been introduced as a routine acceptance checkup/test for produce, let alone for quality assessment of loads containing large quantities of crop.

There therefore remains a need for devices and methods for large scale non-destructive quality analysis of crop loads.

SUMMARY OF THE INVENTION

There is provided herein a system and method for conducting acceptance test without the need for bypass sampling or destructive wet lab analysis, by utilizing hyperspectral imaging. According to some embodiments, the herein disclosed system and method includes/is based on a hyperspectral camera, installed to move above and/or along a truck dump bed or an open container or a crate containing raw produce, thereby enabling rapid scanning of the produce, which in conjunction with advanced image analysis, advantageously provide real time quality control of the produce.

Furthermore, it was advantageously shown that adding additional sensors to the system, such as, but not limited to temperature sensor, surface texture sensor, and shape sensor (by using for example LIDAR systems) as well as RGB imagining as well to enrich the hyperspectral imaging data; and applying AI, deep/machine learning and/or sensor fusion techniques on the data provides robust prediction models regarding a current state/quality of the produce as well as future parameters such as time to ripeness, time to decay etc.

Advantageously, the herein disclosed system allows real-time, non-destructive quality assessment of large quantities of raw produce and optionally also a spatial distribution/degree of homogeneity of the raw produce. The latter is particularly important if the growth conditions, processing/handling, storing conditions etc. of the raw produce differs within a load. As a non-limiting example part of the load may have been exposed to the sun during growth, while at the same time other parts of the load has been shaded of from the sun.

As a further advantage, the system is specially configured to scan large area of produce in order to comply with large loads of produce prior to the produce being supplied to warehouse/packinghouse/winery/cannery etc. The produce load can advantageously be shipped to the checkpoint in diverse containers from complete truck dump beds, to containers, bins, crates or boxes, while still allowing representative sampling and data acquisition, in real time (e.g. within seconds or minutes), in order to ensure the quality of the load.

Moreover, the herein disclosed large-scale evaluation system enables determining internal and external attributes 20 times faster than existing methods, with a capacity of about 1 million kg and a percentage brix deviation of no more than 0.2%.

According to some embodiments, there is provided a system for imaging-based quality assessment of raw produce loads, the system comprising: an imaging structure comprising a mounting beam, comprising a measurement chamber including: one or more light sources; one or more optical sensors operating in visual and/or non-visual spectra, and one or more additional sensors; wherein the measurement chamber is configured to minimize external light from reaching the one or more camera; and wherein the mounting beam is configured to allow vertical, lateral and/or longitudinal and movement of the measurement chamber.

According to some embodiments, the system further comprises a memory and a processor coupled to the memory programmed with executable instructions, the executable instructions comprising a monitoring component for: controlling the vertical, lateral and/or longitudinal movement of the measurement chamber relative to the mounting beam, so as to position the measurement chamber at a predetermined position relative to produce in the produce load; controlling one or more opto-mechanical parameters of the one or more optical sensors, the opto-mechanical parameters selected from: a field of view of the one or more optical sensors, exposure time, aperture, gain, sensitivity, frame rate and any combination thereof; controlling a position, orientation, light projection and/or light intensity of the one or more light sources; triggering signal acquisition by the one or more optical sensors and the one or more additional sensors, upon positioning and/or configuration of the imaging chamber, the one or more optical sensors and/or the one or more light sources; receiving spectral data from the one or more optical sensors and sensor data from the one or more additional sensors; fusing the spectral and sensor data; feeding the fused data into an AI, ML, DL algorithm and/or big-data analytics model, to derive internal and/or external quality attributes of the produce; and producing a report indicating the derived internal and/or external quality attributes.

According to some embodiments, the processor is further configured to identify movement of the container relative to the mounting beam and to time the signal acquisition to the identified movement.

According to some embodiments, the one or more additional sensors is selected from a distance sensor, a lidar sensor, a depth sensor, a temperature sensor, an ultrasonic sensor, fluorescence sensor, X-ray sensor, XRF (X-ray fluorescence) sensor, MRI sensor, dielectric sensor, or any combination thereof. Each possibility and combinations of possibilities is a separate embodiment.

According to some embodiments, the monitoring component is configured to monitor and/or analyze environmental parameters selected from load velocity, light intensity, distance to object of interest, and any combination thereof. Each possibility and combinations of possibilities is a separate embodiment.

According to some embodiments, the monitoring component is configured to monitor and analyze the performance of the system to ensure stable and controlled system performance.

According to some embodiments, the processor is further configured to adjust one or more system parameters, based on the monitored performance, wherein the one or more system parameters are selected from distance to object of interest, exposure time, aperture, frame rate, gain/sensitivity and any combination thereof. Each possibility and combinations of possibilities is a separate embodiment.

According to some embodiments, the processor is configured to monitor the produce load essentially in its entirety. According to some embodiments, the processor is configured to analyze selected samples of the produce in the produce load, wherein the samples are located at various area/parts of the produce load and wherein the analysis comprises extrapolating the sample data to the entire produce load.

According to some embodiments, the extrapolating comprises applying statistical analyses.

According to some embodiments, the one or more optical sensors comprises at least one, at least two, at least three, at least four or at least five hyperspectral cameras. Each possibility is a separate embodiment. According to some embodiments, the one or more optical sensors comprises 2-10 five hyperspectral cameras. According to some embodiments, the one or more optical sensors comprises a camera array including 10-100, 10-50 or 10-25 cameras.

According to some embodiments, the one or more light sources comprises at least one, at least two, at least 3, at least four or at least five halogenic light sources. Each possibility is a separate embodiment. According to some embodiments, the one or more halogenic light sources comprises 2-10 five halogenic light sources. According to some embodiments, the one or more halogenic light sources comprises a hyperspectral camera array including 10-100, 10-50 or 10-25 hyperspectral cameras.

According to some embodiments, triggering the signal acquisition comprises controlling a timing of the signal acquisition.

According to some embodiments, the monitoring component is further configured to calculate a spatial distribution of subsections of the produce with different internal/external attributes and or a degree of homogeneity of the produce in the load.

According to some embodiments, the system further comprises a sensor configured to sense positioning of a load underneath the mounting beam. According to some embodiments, the sensor is a force sensor or a proximity sensor. According to some embodiments, the force sensor may be positioned underneath the mounting beam. According to some embodiments, the proximity sensor may be positioned on the mounting beam, optionally within the measurement compartment.

According to some embodiments, the internal and/or external quality attributes are selected from chemical composition, biochemical composition, physical composition and/or biophysical composition, like dry matter, total soluble solids, sugar content, moisture, acidity, titratable acidity, pH, starch, ascorbic acid, external and/or internal defects, moldiness, decay, pigments, size, shape, texture, contaminants, and any combination thereof. Each possibility and combinations of possibilities is a separate embodiment.

According to some embodiments, the processor is further configured for deriving one or more complex parameters from the one or more of the internal and/or external quality attributes, wherein the one or more complex attribute comprise maturity, ripeness, shelf-life, storability and any combination thereof. Each possibility and combinations of possibilities is a separate embodiment.

According to some embodiments, there is provided a method for assessing a quality of a produce load, the method comprising: entering a load of raw produce into a monitoring station, positioning a measurement chamber at a predetermined position relative to the produce, wherein the measurement chamber comprises one or more light sources, one or more optical sensors and one or more additional sensors, capturing images and collecting data of the produce and retrieving spectral, hyperspectral, image and sensory data therefrom; and fusing the retrieved data; feeding the fused data into an AI, ML, DL algorithm and/or big-data analytics model to derive internal and/or external quality attributes of the produce; and producing a report indicating the internal and/or external quality attributes of the produce, as assed.

According to some embodiments, the one or more additional sensors is selected from a distance sensor, a lidar sensor, a depth sensor, a temperature sensor, an ultrasonic sensor, fluorescence sensor, X-ray sensor, XRF (X-ray fluorescence) sensor, MRI sensor, dielectric sensor, or any combination thereof. Each possibility and combinations of possibilities is a separate embodiment.

According to some embodiments, the one or more internal and/or external parameters are selected from chemical composition, biochemical composition, physical composition and biophysical composition, like dry matter, total soluble solids, sugar content, moisture, acidity, titratable acidity, pH, starch, ascorbic acid, external and/or internal defects, moldiness, decay, pigments, size, shape, texture, contaminants, and any combination thereof. Each possibility and combinations of possibilities is a separate embodiment.

According to some embodiments, the method further comprises deriving one or more complex parameters from the one or more of the internal and/or external quality attributes, wherein the one or more complex attribute comprise maturity, ripeness, shelf-life, storability and any combination thereof. Each possibility and combinations of possibilities is a separate embodiment.

According to some embodiments, the method further comprises moving the measurement chamber, to thereby allow scanning of different areas of the produce. According to some embodiments, the method further comprises moving the produce load relative to the measurement chamber to thereby allow scanning of different areas of the produce.

According to some embodiments, the method further comprises determining a spatial distribution and/or degree of homogeneity of the produce load.

According to some embodiments, the method further comprises detecting, using a sensor, a change in the position of the produce load relative to the measurement chamber and automatically triggering signal acquisition by the one or more optical sensors and the one or more additional sensors.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

In addition to the exemplary aspects and embodiments described above, further aspects and embodiments will become apparent by reference to the figures and by study of the following detailed descriptions.

BRIEF DESCRIPTION OF THE FIGURES

Some embodiments of the disclosure are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the disclosure. For the sake of clarity, some objects depicted in the figures are not drawn to scale. Moreover, two different objects in the same figure may be drawn to different scales. In particular, the scale of some objects may be greatly exaggerated as compared to other objects in the same figure.

In block diagrams and flowcharts, certain steps may be conducted in the indicated order only, while others may be conducted before a previous step, after a subsequent step or simultaneously with another step. Such changes to the orders of the step will be evident for the skilled artisan.

DETAILED DESCRIPTION

Figure 1:
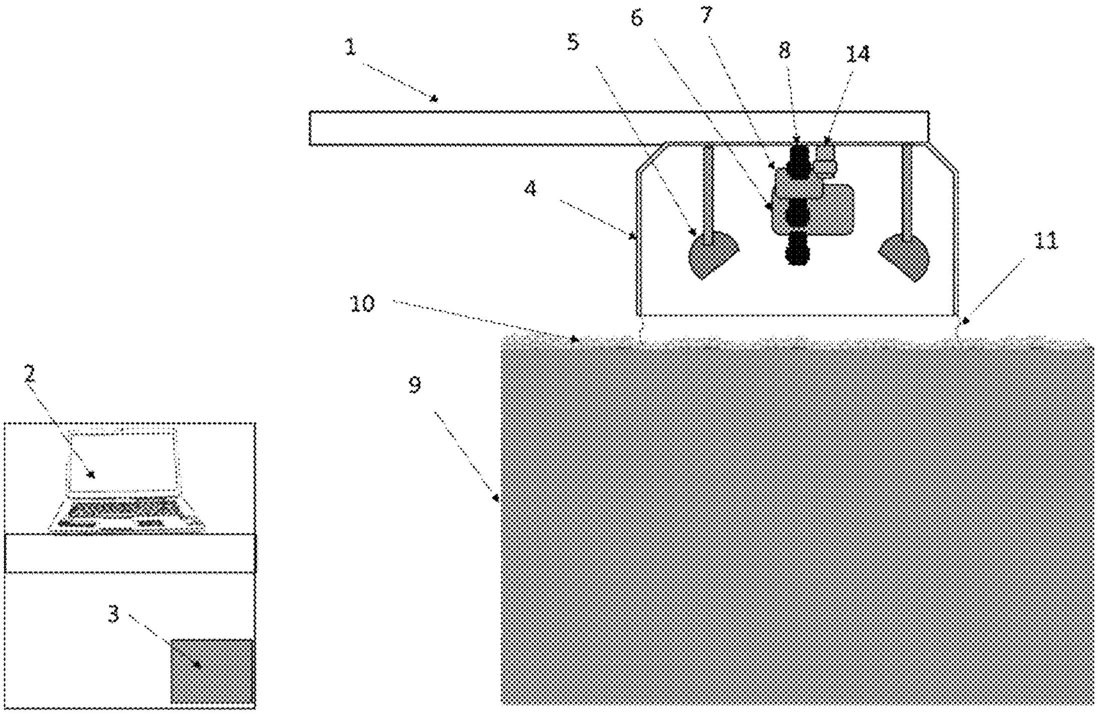
FIG. 1 is a schematic illustration of the herein disclosed large-scale hyperspectral imaging system for analysis of crop loads, according to some embodiments.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

According to some embodiments, there is provided a system for imaging-based quality assessment of produce loads. According to some embodiments, the imaging-based quality assessment comprises hyperspectral imaging. According to some embodiments, the imaging-based quality assessment further comprises RGB imaging.

As used herein the term "hyperspectral imaging" refers to a process including collecting and processing information from across the electromagnetic spectrum to obtain the spectrum for each pixel in the image of a scene. That is, in hyperspectral imaging, the recorded spectra have fine wavelength resolution and cover a wide range of wavelengths. There are three general types of spectral imagers. There are push broom scanners and the related whisk broom scanners (spatial scanning), which read images over time, band sequential scanners (spectral scanning), which acquire images of an area at different wavelengths, and snapshot hyperspectral imagers, which uses a staring array to generate an image in an instant.

As used herein, the term "produce" refers to a farm-produced crop, including fruits, vegetables, grains, oats, etc. More specifically, the term produce preferably refers to fresh products including post-harvest crop.

As used herein, the term "produce load" refers to a large aggregation of produce, such as at least 0.1 kg, at least 0.5 kg, at least 1 kg, at least 10 kg, at least 100 kg produce, at least 500 kg, at least 1000 kg, at least 5000 kg, or at least 10,000 kg. Each possibility is a separate embodiment. According to some embodiment, the produce load may be a crate, box, container, a truck load or the like.

As used herein, the terms "in real-time" and "on-the-fly", may be used interchangeably and refer to a produce evaluation which does not require destruction of the produce or lab test results. According to some embodiments, a real-time evaluation of an entire produce load may be completed in less than 1 hour, less than 30 min, less than 20 min, less than 15 minutes or less than 10 minutes or less than 5 minutes or less than 1 min.

According to some embodiments, the system includes an imaging structure configured to positioning one or more optical sensors above a produce load to allow evaluation thereof. According to some embodiments, the imaging structure includes a mounting beam, wherein the mounting beam is configured to allow vertical, lateral and/or longitudinal movement of an associated measurement chamber relative to the mounting beam, as further described herein. Each possibility is a separate embodiment.

As used herein, the term "movement of a measurement chamber" may refer to movement of the entire measurement chamber or parts thereof. Each possibility is a separate embodiment.

According to some embodiments, the associated measurement chamber contains one or more light sources and one or more optical sensors working in the visual, the non-visual spectra or both. Each possibility is a separate embodiment. According to some embodiments, the imaging chamber is configured to minimize external light from reaching the one or more optical sensors.

According to some embodiments, the system further includes one or more additional sensors, such as but not limited to a distance sensor, a lidar sensor, a depth sensor, a temperature sensor, an ultrasonic sensor, fluorescence sensor, X-ray sensor, XRF (X-ray fluorescence) sensor, Mill sensor, dielectric sensor, or any combination thereof. Each possibility is a separate embodiment. According to some embodiments, at least some of the one or more additional sensors may be positioned within the imaging chamber.

According to some embodiments, the system includes a memory; and a processor coupled to the memory, programmed with executable instructions, the executable instructions comprising a monitoring component for (order not limiting):

a. controlling vertical, lateral and/or longitudinal movement of the mounting beam relative to the lifting beam (and/or vis versa) so as to position the imaging chamber at a predetermined position relative to the produce in the produce load.
b. controlling opto-mechanical parameters of the one or more optical sensors, the opto-mechanical parameters selected from exposure time, aperture, gain, sensitivity, frame rate or any combination thereof and the like. Each possibility is separate embodiment.
c. controlling the position, orientation, light projection and/or light intensity of the one or more light sources.
d. triggering signal acquisition by the one or more optical sensors and optionally by the one or more additional sensors upon positioning and/or configuration of the imaging chamber, the one or more optical sensors and/or the one or more light sources. According to some embodiments, triggering the operation of the one or more optical sensors comprises controlling the timing of the signal acquisitions.
e. receiving visual and/or non-visual data from the one or more optical sensors and additional sensors,
f. combining/fusing the data and feeding it to an analyzing algorithms. According to some embodiments, the fusion procedure comprises combination of sensor outputs and the combination of reference parameters. According to some embodiments, linear and non-linear regression or classification methods were applied for model establishment.
g. analyzing the data from all the optical sensors and sensors and/or on the fused data by applying artificial intelligence (AI), machine learning (ML), deep learning (DL) and data analysis algorithms thereon, to derive internal and/or external quality attributes of the produce. Non-limiting examples of quality attributes include visual appearance (freshness, color, shape, size, decay, defect), texture (like turgidity, crispness, firmness), nutritional value (like vitamin A and C) and flavor (like taste and smell) or any combination thereof. Each possibility is a separate embodiment. According to some embodiments, the internal and/or external quality attributes are selected from chemical, biochemical, physical and biophysical composition like dry matter, total soluble solids, sugar/s content, moisture, acidity, titratable acidity, pH, starch, ascorbic acid, external and/or internal disorder, moldiness, decay, pigments, size, shape, texture, contaminants, etc. Moreover, the combination of the above's and or more complex attributes like maturity, ripeness, shelf-life, storability and alike.
h. producing a report indicating the internal and/or external quality attributes of the produce, as derived from the AI, ML, DL and/or big data analysis.

According to some embodiments, the processor is further configured to identify movement of the container relative to the measurement chamber. According to some embodiments, the processor is further configured to time the signal acquisition by the one or more optical sensors and/or additional sensors to the identified movement.

According to some embodiments, the vertical, lateral and/or longitudinal movement of the measurement chamber relative to the produce enables imaging of different areas of the produce and/or different layers/depths of the produce in the produce load.

According to some embodiments, the monitoring component may be further configured to calculate a spatial distribution of subsections of the produce with different internal/external attributes and or a degree of homogeneity of the produce in the container. This may advantageously allow identification of produce of different quality within the produce load.

According to some embodiments, the monitoring component includes algorithms capable of performing tasks, such as, but not limited to:

a. monitoring and analyzing environmental parameters such as, but not limited to: load velocity, light intensity, distance to the object of interest and any combination thereof. Each possibility is a separate embodiment.
b. monitoring and analyzing the performance of components of the system, such as: motors, cameras, lenses, and/or additional sensors.
c. control and adjustment of system parameters to assist data acquisition and analysis. This includes, but is not limited to: distance to the object of interest, camera/sensor exposure, aperture, frame rate, gain/sensitivity and any combination thereof. Each possibility is a separate embodiment.
d. identifying and analyzing every single fruit or area/aggregation according to the requirements of the customer in the cameras and sensors' field of view.
e. running statistical analysis on the analysis results.
f. communicating the results of the above to a software system of a customer.

According to some embodiments, the one or more optical sensors comprise at least 2, at least 3, at least 4 or at least 5 optical sensors. Each possibility is a separate embodiment. According to some embodiments, the one or more optical sensors comprises a hyperspectral imaging camera/system.

According to some embodiments, the one or more light sources comprises one or more light sources, e.g. 1, 2, 3, 4, 5, 6, 7, 8, 9, 10 or more light sources. Each possibility is a separate embodiment. According to some embodiments, the one or more light sources may be spaced apart by a predetermined, preferable equal distance from one another.

According to some embodiments, at least one of the one or more light sources is a halogen light source. As used herein, the terms "halogen light source" and "halogen lamp" may be used interchangeably and refer to lamp that produces a spectrum of light, preferably from near ultraviolet to deep into the infrared spectrum. According to some embodiments, the halogen light source may be a continuous light source, i.e. include the entire spectrum. According to some embodiments, the halogen light source may be a non-continuous light source, including only portions of the entire spectrum or operating in a pulsating mode, such as but not limited to strobe light. According to some embodiments, all of the one or more light sources are halogen light sources.

According to some embodiments, the one or more optical sensors further comprise an RGB camera. According to some embodiments, the one or more optical sensors further comprise a VIS-NIR or SWIR spectrophotometer. According to some embodiments, the spectrophotometer has a spectral range of 350-1000 nm or 900-1700 nm or 300-2500 nm.

According to some embodiments, the system may further include a sensor configured to sense positioning of a produce load underneath the mounting beam. According to some embodiments, the sensor is a proximity sensor. According to some embodiments, the sensor is a force sensor.

Reference is now made to FIG. 1, which schematically illustrates the herein disclosed system for imaging-based quality assessment of produce loads. The system includes a mounting beam (1), attached to which is a measurement compartment (4) including a variety of optical sensors and other sensors, here illustrated: , an RGB camera (6), a hyperspectral camera (7), a laser-imaging-detection-and-ranging (LIDAR) device (8), a temperature sensor (14). Measurement compartment (4) further includes light sources (5). According to some embodiments, measurement compartment (4) may further include a shade, cover or curtain (11) configured to screen off a sampling area from outside light. According to some embodiments, measurement compartment (4) is functionally connected to a processor (2) (such as but not limited to a PC), which in turn is configured to fuse the signals obtained from the various sensors and to apply AI, ML, DL modules thereon, to extract external and internal quality attributes of the produce. According to some embodiments, measurement compartment (4) and/or processor (2) are functionally connected and to a power supply (3). Measurement compartment (4) is configured to be positioned above a produce (9) here contained in a container (10) so as to assess/evaluate the quality of the produce on-the-fly, i.e., without requiring removal of produce (9) from container (10). According to some embodiments, the system is configured to sample various vertically (at different depths of the container), laterally and/or longitudinally spaced apart areas of the produce. Each possibility is a separate embodiment.

Figure 2:
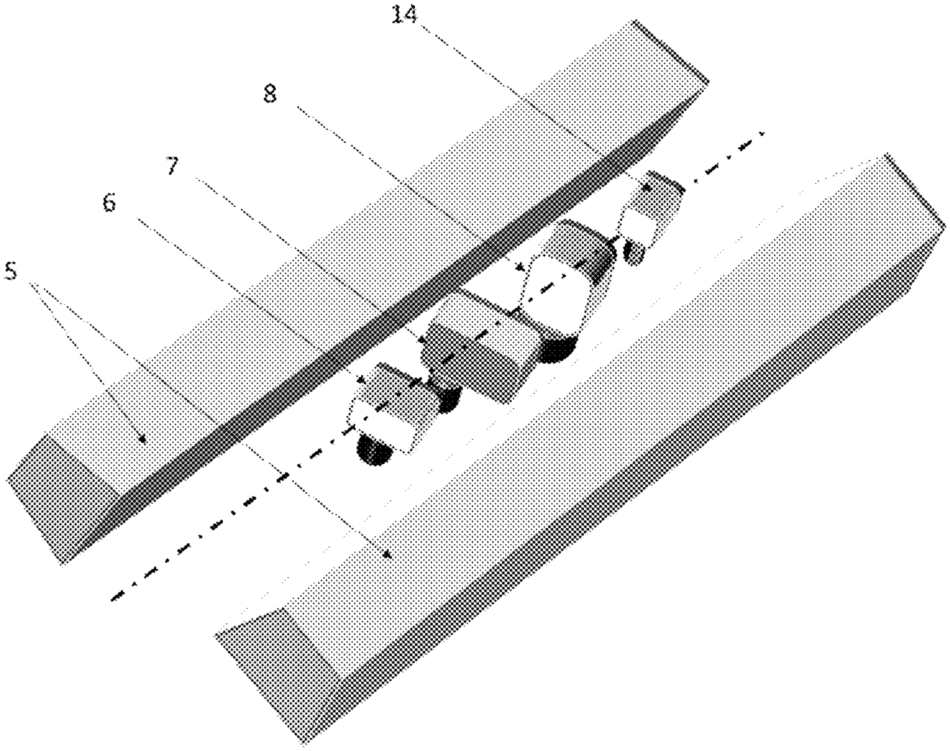
FIG. 2 is a schematic illustration of the herein disclosed hyperspectral imaging chamber and sensor setup, for analysis of crop loads, according to some embodiments.

Reference is now made to FIG. 2, which schematically illustrates measurement compartment (4) in further detail.

According to some embodiments, measurement compartment (4) includes at least two light sources (5). According to some embodiments, light sources (5) are halogen lamps. According to some embodiments, the two lamps may have an elongated shape. According to some embodiments, the at least two light sources (5) may be positioned such that the entire area examined (the area positioned underneath measurement compartment (4) and shielded off by curtain (11)) is illuminated essentially homogenously. According to some embodiments, the position of the at least two light sources (5) may be adjustable. For example, according to some embodiments, the vertical or other positioning of the light sources within measurement compartment (4) may be adjustable. This may for example enable generating a desired distance between the light source and the produce examined. As another example, and according to some embodiments, the angle of the light source may be adjustable.

Measurement compartment (4) further includes optical and non-optical sensors. According to some embodiments, measurement compartment (4) preferably includes one or more hyperspectral cameras, such as hyperspectral camera (7) configured for hyperspectral imaging of produce in the area of examination. According to some embodiments, the position of hyperspectral camera (7) and/or of its focus and field of view are adjustable.

According to some embodiments, measurement compartment (4) further includes one or more RGB cameras, such as RGB camera (6). According to some embodiments, RGB camera (6) is primarily configured to image the color and/or color homogeneity and/or external quality of the produce. According to some embodiments, the position of RGB camera (6) and/or of its focus and field of view are adjustable.

According to some embodiments, measurement compartment (4) further includes one or more LIDAR sensors, such as LIDAR (8). According to some embodiments, LIDAR (7) is primarily configured for determining the shape characteristics of the produce, by targeting the produce with a laser and measuring the time for the reflected light to return to the receiver, thereby allowing a spatial, optionally 3D-scanning of the produce.

According to some embodiments, measurement compartment (4) further includes a temperature sensor, such as temperature sensor (14) configured to measure the temperature of the produce. According to some embodiments, temperature sensor (14) is primarily used for correction of the spectral changes identified by the hyperspectral imaging. According to some embodiments, the spectral fingerprint of the produce is determined based on the data obtained from the temperature sensor.

According to some embodiments, measurement compartment (4) further includes a distance sensor (not shown) configured to measure the distance between a position within measurement compartment (4) and the produce.

According to some embodiments, measurement compartment (4) further includes a depth sensor (not shown) configured to measure the depth of the container load.

According to some embodiments, additional sensors such as an ultrasonic sensor, a fluorescence sensor, an X-ray sensor, an XRF (X-ray fluorescence) sensor, an MRI sensor, a dielectric sensor, or any combination thereof. Each possibility is a separate embodiment. According to some embodiments, at least some of the additional sensors (e.g., the X-ray, ultrasonic and MM sensors) may be used to identify internal structures of the produce, such as but not limited to seeds, kernels, foreign objects, decay, and the like. According to some embodiments the deep learning algorithm may be trained to differentiate between different types of internal structures, such as but not limited to differentiation between a kernel and a foreign object, or between decay and fertilization. According to some embodiments, at least some of the additional sensors (e.g., the fluorescent, XRF and UV sensors) may be configured for identification of non-organic and/or organic compounds such as but not limited to fertilizers, pesticides, herbicides, fungicides, insecticides, metal compounds (originating from foreign objects or as a natural resource of the produce) One or several of these additional sensors can be mounted in the measurement compartment and their data/signals integrated into the AI, ML, DL and big data analysis and models.

Figure 3:
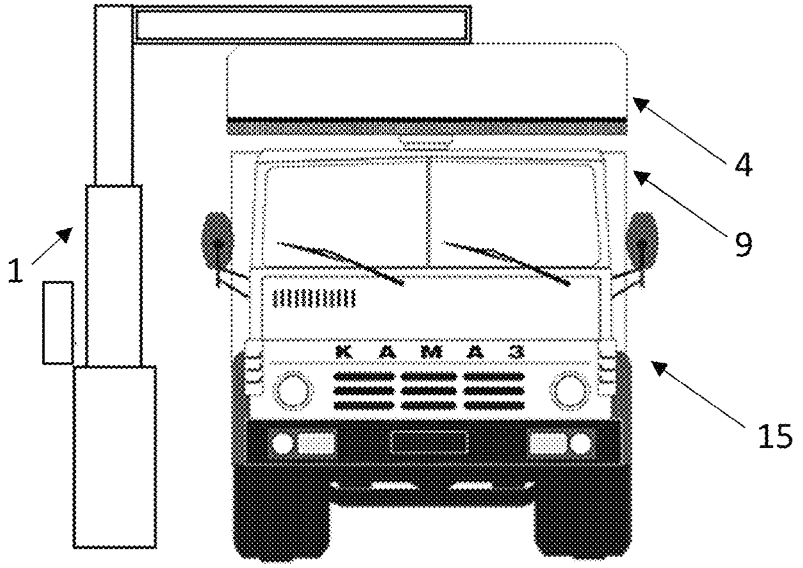
FIG. 3 schematically illustrates an imaging structure during analysis of a truck dump bed, according to some embodiments.

Reference is now made to FIG. 3, which schematically illustrates a mounting beam, such as mounting beam (1) with a measurement compartment, such as measurement compartment (4). Measurement compartment (4) includes at least a hyperspectral camera and one additional optical and/or non-optical sensor. In this embodiment, the position of mounting beam (1) and of measurement compartment (4) is constant and configured for evaluating a produce while the produce load (here the truck (15)) is advancing relative to measurement compartment (4). According to some embodiments, measurement compartment (4) may be moved vertically (up and down) on mounting beam (12) to adjust the distance of measurement compartment (4) relative to the produce.

Figure 4:
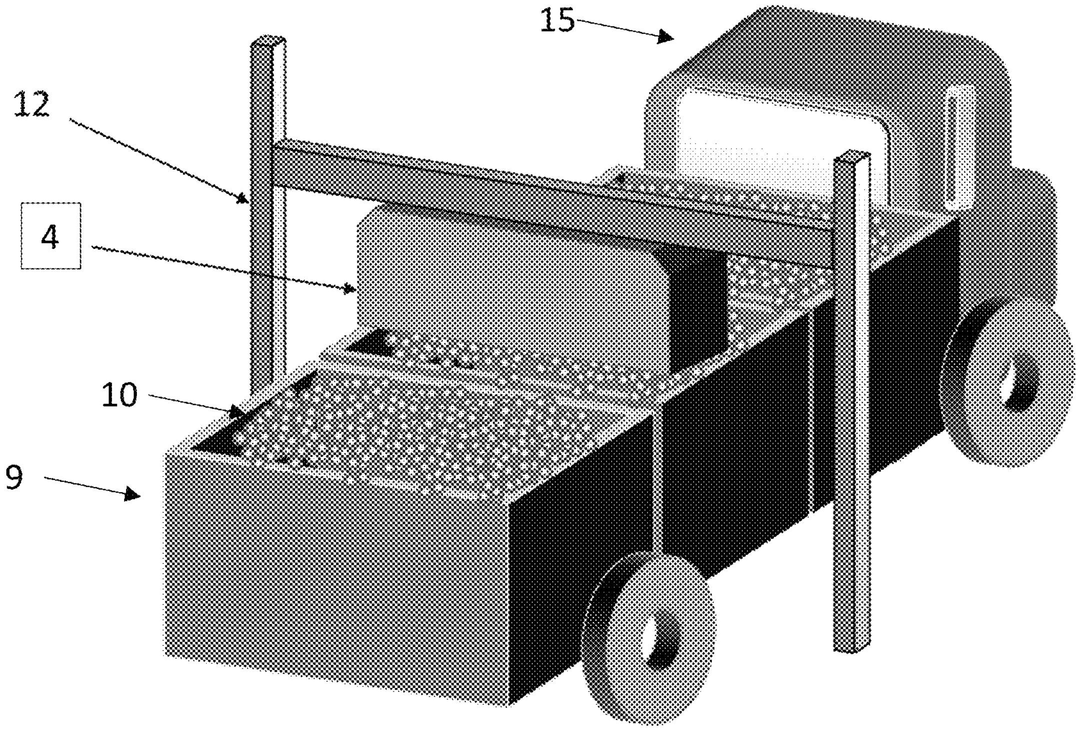
FIG. 4 schematically illustrates a movable imaging structure during analysis of a truck dump bed, according to some embodiments.

Reference is now made to FIG. 4, which schematically illustrates a mounting beam, such as mounting beam (1) with a laterally movable measurement compartment, such as measurement compartment (4). Measurement compartment (4) includes at least a hyperspectral camera and one additional optical and/or non-optical sensor, as detailed for example in FIG. 2. However, in this embodiment, measurement compartment (4) can be moved/slid laterally thereby allowing scanning of wider areas of the produce load, without moving the produce. According to some embodiments, measurement compartment (4) may further be moved vertically (up and down) on mounting beam (12) to adjust the distance of measurement compartment (4) relative to the produce.

Figure 5:
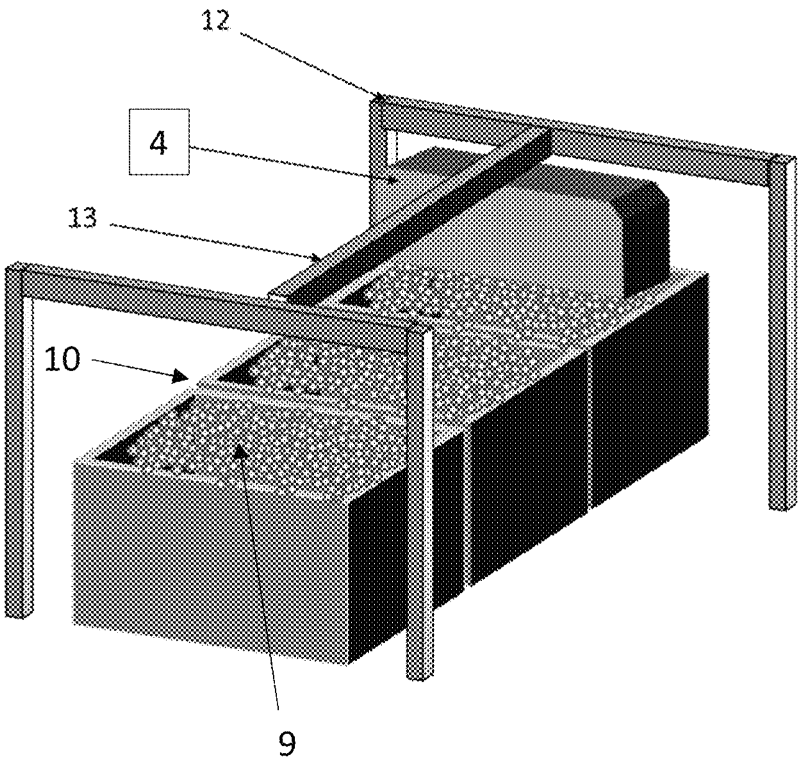
FIG. 5 schematically illustrates an imaging structure including a movable imaging chamber, during analysis of a truck dump bed, according to some embodiments.

Reference is now made to FIG. 5, which schematically illustrates a mounting beam (12) with a longitudinally movable measurement compartment (4). As before, measurement compartment (4) may include at least a hyperspectral camera and one additional optical and/or non-optical sensor, as detailed for example in FIG. 2. However, in this embodiment, measurement compartment (4) can be moved/slid longitudinally (e.g. upon instructions from a processor) on a longitudinal beam (13) of mounting beam (12), thereby enabling assessment of the truck dump bed (9) without movement of the truck (15). According to some embodiments, measurement compartment (4) can be moved/slid both laterally and longitudinally. According to some embodiments, measurement compartment (4) may be moved vertically (up and down) on mounting beam (12) to adjust the distance of measurement compartment (4) relative to the produce.

Figure 6:
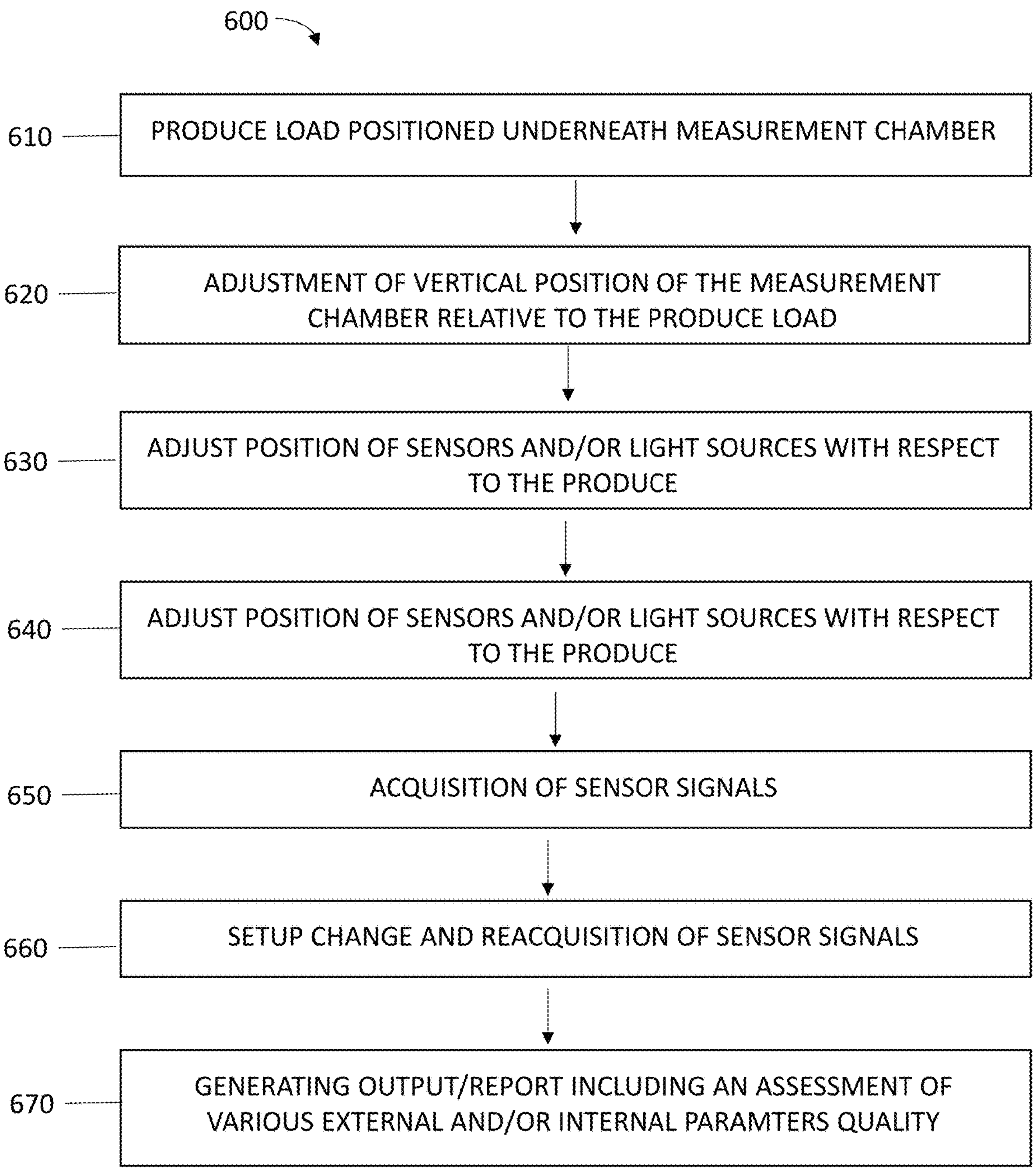
FIG. 6 is an illustrative flow chart of the herein disclosed method for assessment of internal and external quality attributes of produce, according to some embodiments.

Reference is now made to FIG. 6 which is an illustrative method 600 for real-time evaluation of a produce load, according to some embodiments. It is understood that at least some of the steps may be executed simultaneously or in a different order and that the depicted sequential order of the steps is illustrative only.

In step 610 a produce load (e.g., a truck dump bed including grapes entering a winery) is positioned underneath a measurement chamber, such as measurement chamber (4) described in FIG. 2. According to some embodiments, the entering of the produce load and/or of the truck containing the produce load may be automatically detected. For example, a distance sensor may be included, which distance sensor is configured to identify presence of an object above ground level. As another non-limiting example, a force sensor, positioned on the ground underneath the measurement chamber, may sense placement of a load.

In step 620, if required, the measurement chamber is moved vertically (up/down) relative to the mounting beam to which it is attached, in order to obtain a predetermined desired distance from the produce. According to some embodiments, adjusting the position comprises triggering a vertical movement mechanism via a functionally associated processor. According to some embodiments, the predetermined position depends on several factors, like the type of produce etc. According to some embodiments, the predetermined position depends on which quality parameters are evaluated. According to some embodiments, the method includes inputting to the processor the type of produce evaluated and/or the quality parameters to be assessed. According to some embodiments, based upon the input, a preferred distance from the produce can be automatically calculated and executed. Additionally or alternatively, the desired distance may be determined automatically based on signals obtained from a distance sensor configured to measure a vertical position of the measurement chamber relative to the produce. According to some embodiments, the vertical movement of the measurement chamber may be manually operated, optionally in conjunction with guidance/instructions obtained from the processor, based on the calculated optimal position. According to some embodiments, the optimal distance between the measurement chamber and the produce load may be set based on an initial hyperspectral signature determined for the produce. According to some embodiments, the optimal distance between the measurement chamber and the produce load may be set based on an initial signal acquisition conducted on the produce. According to some embodiments, the optimal distance between the measurement chamber and the produce load may be set based on an initial optical response of the produce.

In step 630, the position (physical or measurement field) of the sensors and/or the light sources of the measurement chamber may be adjusted to an optimal position vis-à-vis the produce. According to some embodiments, the optimal position of the sensors may depend on the type of produce evaluated and/or the quality parameters to be assessed. According to some embodiments, the method further includes inputting to the processor the type of produce evaluated and/or the quality parameters to be assessed. According to some embodiments, based upon the input a preferred position of the sensors and/or light sources can be automatically calculated and executed. Additionally or alternatively, the preferred position of the sensors and/or light sources may be determined automatically, based on signals obtained from a distance sensor configured to measure the distance from an initial (fallback) position of the sensors. According to some embodiments, the positioning of the sensors and/or light sources may be executed manually, optionally in conjunction with guidance/instructions obtained from the processor, based on the calculated optimal position thereof. According to some embodiments, the optimal position of the sensors and/or light sources may be set based on an initial hyperspectral signature determined for the produce. According to some embodiments, the optimal position of the sensors and/or light sources may be set based on an initial signal acquisition conducted on the produce. According to some embodiments, the optimal position of the sensors and/or light sources may be set based on an initial optical response of the produce.

In step 640, one or more operation parameters of the sensor(s) and/or light source(s) may optionally be configured. Non-limiting examples of such parameters include light intensity of the light source(s), the angle of the emitted light, exposure time, aperture, gain, sensitivity, frame rate or the like of the hyperspectral and/or other cameras etc. According to some embodiments, the operation parameters may depend on the type of produce evaluated and/or the quality parameters to be assessed. According to some embodiments, the method further includes inputting to the processor the type of produce evaluated and/or the quality parameters to be assessed. According to some embodiments, based upon the input the preferred operation parameters can be automatically calculated and set. Additionally or alternatively, the operation parameters may be determined automatically, based on signals obtained from a distance sensor configured to measure the distance from an initial (fallback) position of the sensors. Additionally or alternatively, the operation parameters may be determined automatically, based on signals obtained from a temperature sensor. According to some embodiments, the optimal operation parameters may be set based on an initial hyperspectral signature determined for the produce. According to some embodiments, the optimal operation parameters may be set based on an initial signal acquisition conducted on the produce. According to some embodiments, the optimal operation parameters may be set based on an initial optical response of the produce.

In step 650, signal acquisition is performed. According to some embodiments, the produce is scanned by the hyperspectral camera, and at least one additional sensor, such as an RGB camera, a temperature sensor, an ultrasonic sensor and the signals transferred to the processor for analysis as further elaborated in FIG. 7. According to some embodiments, the signal acquisition comprises controlling operation e.g. turning on the light sources.

In step 660, the signal acquisition may be continued, while changing one or more features of the setup. As a non-limiting example, a same area may be rescanned upon vertical replacement of the measurement chamber, in order to scan different depths of the produce load. As another non-limiting example, different areas of the produce load may be scanned by lateral or longitudinal movement of the measurement chamber or by movement of the produce load. As another non-limiting example, different quality attributes may be evaluated by changing one or more parameters of the sensors/light sources. According to some embodiments, the newly acquired signals may be transferred to the processor where they may be integrated into the previously acquired signals (e.g. for providing parameters such as produce homogeneity, average expected shelf life etc.) or serve as basis for new calculations, e.g. of additional quality attributes.

In step 670, an output, for example in the form of a QA report may be produced, the report indicating the internal and/or external quality parameters assessed/estimated for the produce load. According to some embodiments, the report includes at least one internal and at least one external quality attribute, all obtained via the hereindisclosed non-destructive quality assessment method. According to some embodiments, the report includes at least two internal and at least two external quality attributes, all obtained via the hereindisclosed non-destructive quality assessment method. According to some embodiments, the report includes a plurality (e.g. at least 5, or at least 10 quality attributes) of internal and external quality attributes (e.g. at least 5, or at least 10 external/internal quality attributes), all obtained via the hereindisclosed non-destructive quality assessment method.

Figure 7:
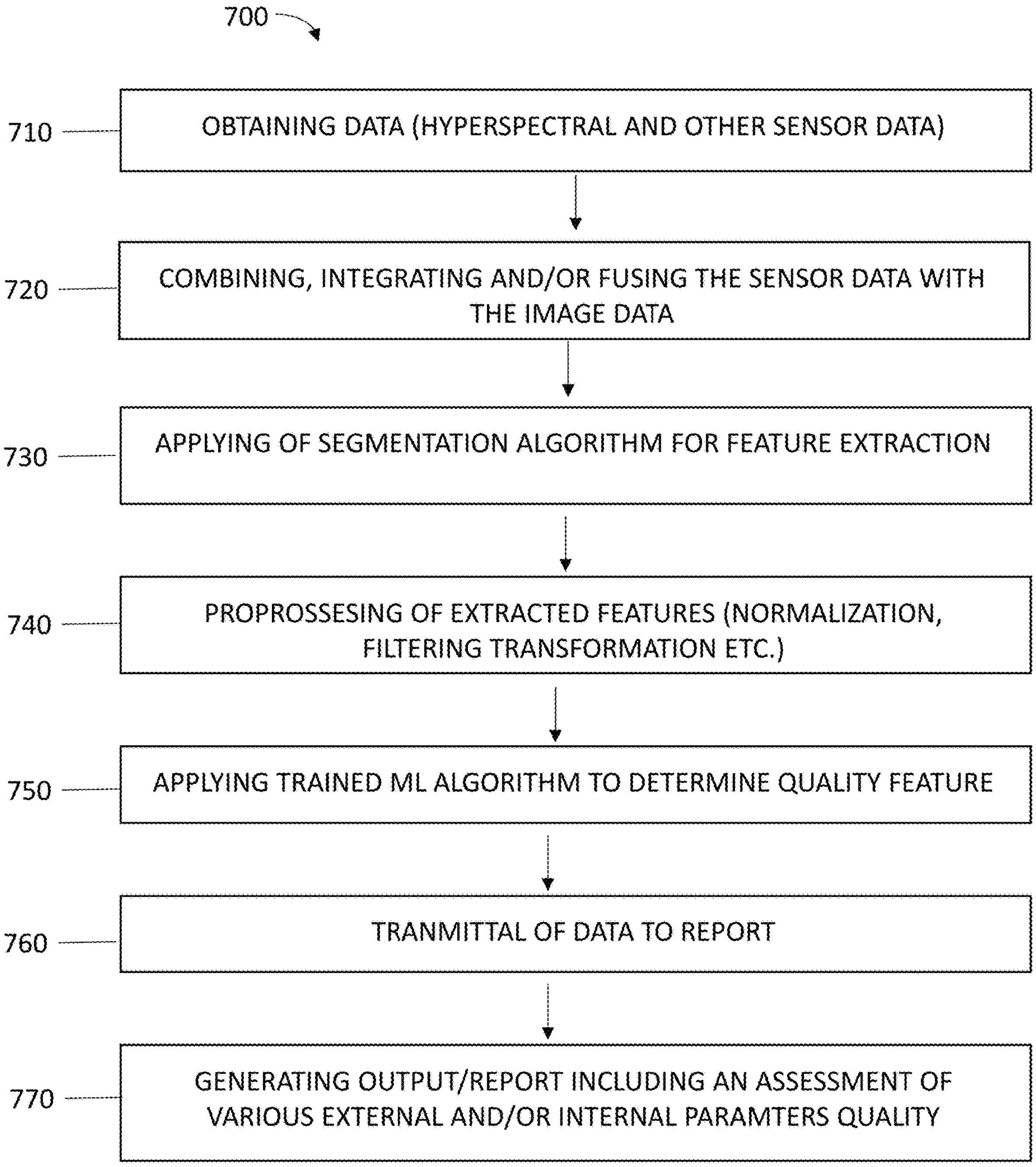
FIG. 7 is an illustrative flow chart of the herein disclosed method for assessment of internal and external quality attributes of produce, according to some embodiments.

Reference is now made to FIG. 7, which is an illustrative method 700 for the assessment/estimation of internal and/or external quality attributes, based on the signal acquired (e.g. as set forth with respect to FIG. 6. It is understood that at least some of the steps may be executed simultaneously or in a different order and that the depicted sequential order of the steps is illustrative only.

In step 710, hyperspectral images, other image data and sensor data (obtained from the hyperspectral cameras and the additional sensors) are assembled. In step 720, the other image and sensory data is then combined in and/or integrated with and/or fused with the hyperspectral images to obtain a data cube. In step 730, a segmentation algorithm is optionally applied in order to extract the relevant information from the data cube. In step 740, normalization and/or filtering and/or preprocessing and/or transformation of the data cube can likewise be conducted in order to extract the desired information. In step 740, a trained or otherwise defined AI, ML, DL algorithm is then applied on the extracted data cube in order to determine/calculate the desired quality feature. In step 750, the determined/calculated quality features are then transferred to the reporting tool.

Figure 8:
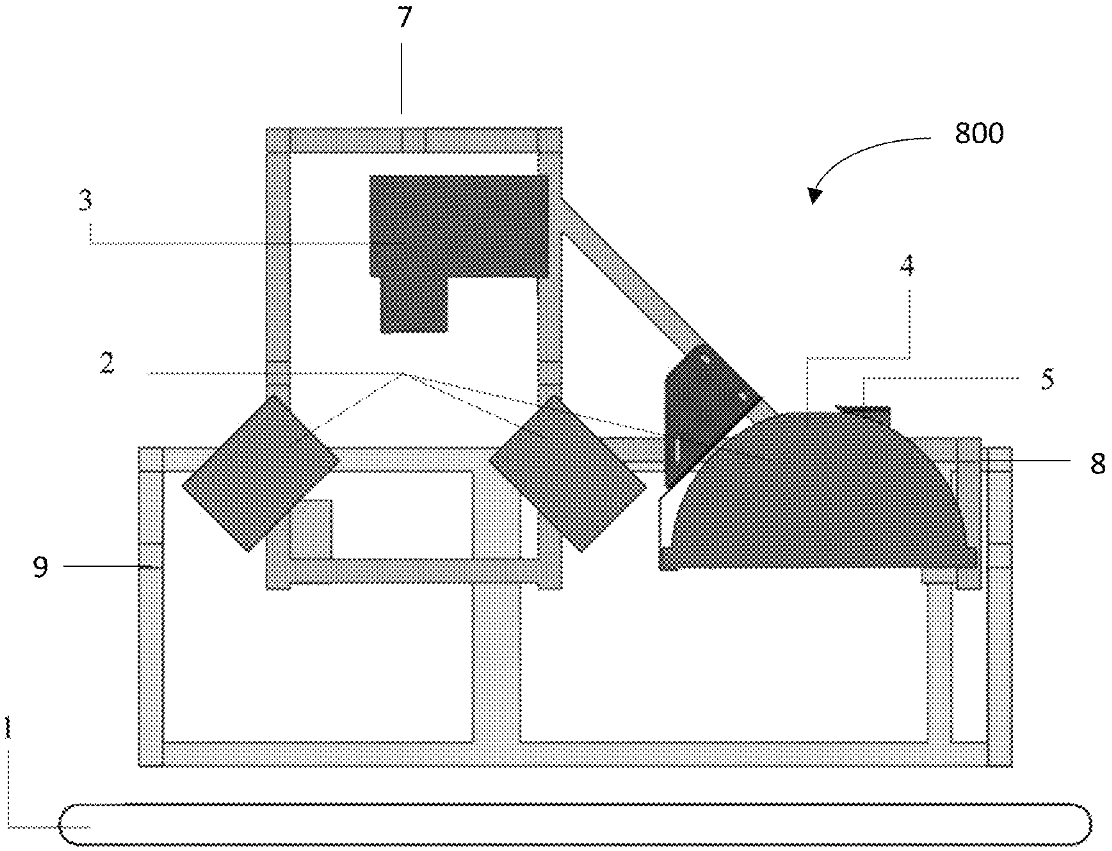
FIG. 8, schematically illustrates large-scale hyperspectral imaging system for analysis of crop loads, according to some embodiments.

Reference is now made to FIG. 8, which schematically illustrates the herein disclosed system 800 for small scale imaging-based quality assessment of produce loads. The system is here positioned above a conveyor belt (1) and includes illumination sources (preferably continuous or non-continuous halogenic) light sources (2), a hyperspectral camera (3) an RGB camera as well as one or more additional sensors (5) as essentially described herein. Advantageously, light sources (2) and hyperspectral camera (3) may be attached to a first scaffold structure (7) and RGB camera to a second scaffold structure (8).

According to some embodiments, first scaffold structure (7) is configured to allow lateral and/or vertical movement of illumination sources (2) and/or hyperspectral camera (3) to allow optimization of their relative position and of their position vis-à-vis produce on conveyor belt (1). According to some embodiments, second scaffold structure (8) is configured to allow lateral and/or vertical movement of RGB camera (4) and/or additional sensors (5) to allow optimization of their position vis-à-vis the produce.

According to some embodiments, first scaffold (7) and second scaffold (8) are further interconnected so as to allow adjusting the distance therebetween.

System 800 further includes a third scaffold structure (9), configured to allow longitudinal movement of first scaffold (7) and second scaffold structure (8), while maintaining their lateral position. This may advantageously allow scanning of different areas of the produce without movement of the container. According to some embodiments, system 800 is further configured to sample various vertically spaced apart areas of the produce.

It is understood the system 800 is functionally connected to a processor, such as, but not limited to a PC (not shown), which in turn is configured to fuse the signals obtained from the hyperspectral camera (3), RGB camera (4) and additional sensors (5) sensors and to apply AI, ML, DL modules thereon, to extract external and internal quality attributes of the produce.

The following examples are presented in order to more fully illustrate some embodiments of the invention. They should in no way be construed, however, as limiting the broad scope of the invention. One skilled in the art can readily devise many variations and modifications of the principles disclosed herein without departing from the scope of the invention.

EXAMPLES

Example 1—Wine Grape Evaluation on Truck Load

Figure 9:
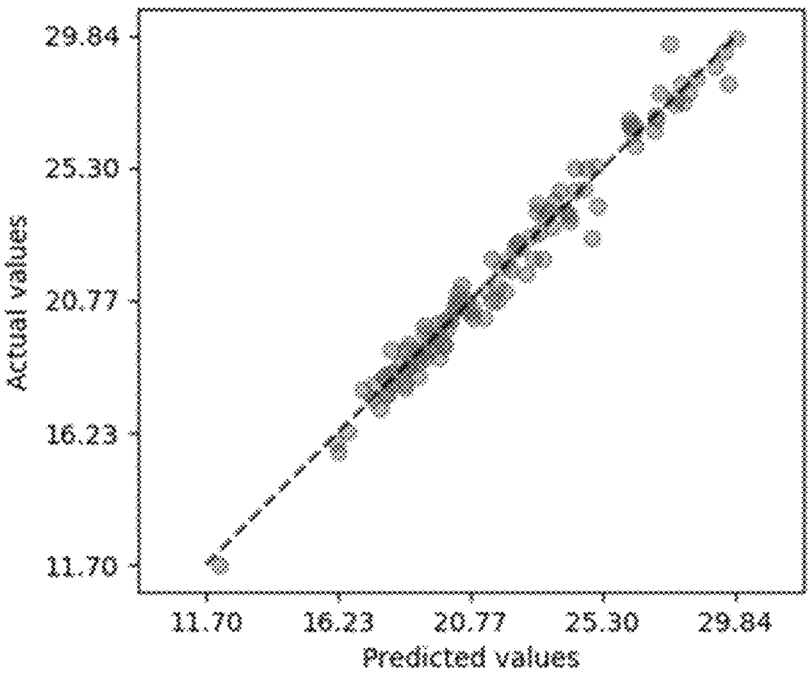
FIG. 9, shows the total soluble solids (TSS) in wine grape, measured vs predicted using the herein disclosed system and method directly on a truck load. Each point illustrated is an independent sample/area of interest.

Total Soluble Solids (TSS) content prediction in a truck load of wine grapes was performed by hyperspectral imaging using the hereindisclosed large-scale evaluation system with adjustable measurement compartment. The measurement compartment was positioned by lateral and vertical movement to an optimal scanning position above the load, based on the reading of a proximity sensor positioned in the measurement chamber. During the scanning process in this example, the measurement compartment was longitudinally stationary, and the truck load was moved. On the surface of each area to be scanned, several areas of interest (AOI) locations were selected and marked. After the scanning, samples were taken from each particular AOI, and TSS were measured by destructive tests. In short, wine grape berries were juiced and three to five drops of the juice were taken to determine TSS content with a digital refractometer (Atago, Japan). The TSS content was expressed in Brix%. Altogether 500 samples were taken and used in the ML training procedure. The test result of the ML model on 150 AOI is depicted in FIG. 9, where the non-destructively predicted TSS content based on the hyperspectral imaging of each sample is shown in relation to the destructively measured TSS content. The ML model prediction error is 0.6 Brix%.

As seen from the FIG. 9, the herein disclosed hyperspectral imaging system provided a reliable prediction of actual TSS content.

Example 2—Bell Pepper Evaluation

Total Soluble Solids (TSS) content prediction in a load of bell pepper trays (150×250 mm) was performed by hyperspectral imaging using the hereindisclosed small-scale evaluation system with adjustable measurement compartment. The measurement compartment was positioned by lateral and vertical movement to an optimal scanning position above the load, based on the reading of a proximity sensor positioned in the measurement chamber.

Figure 10:
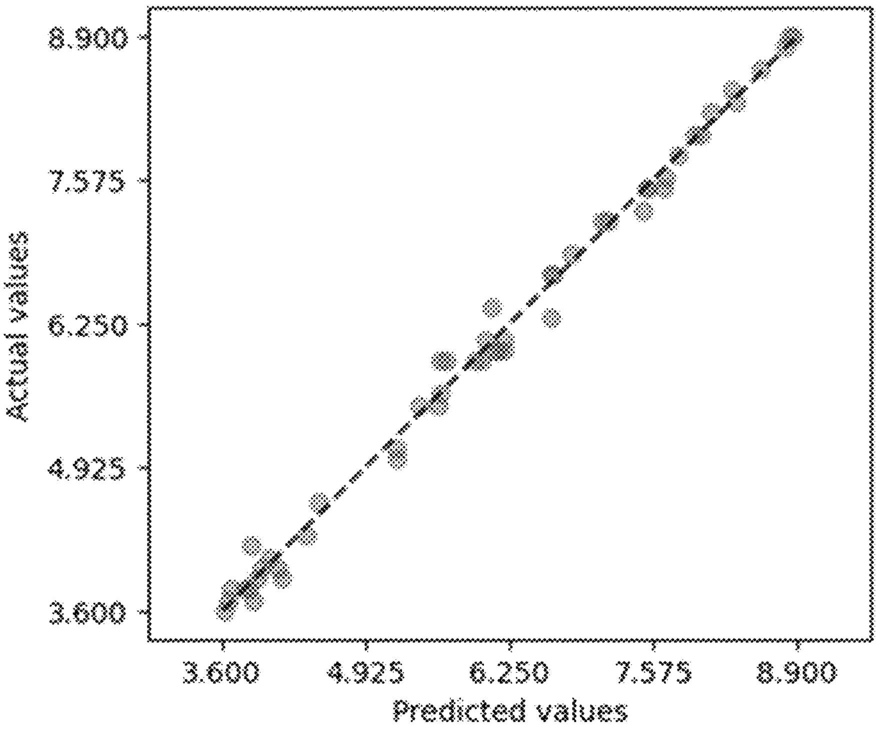
FIG. 10, shows the total soluble solids (TSS) in bell peppers, measured vs predicted using the herein disclosed system and method. Each point illustrated is an independent sample/area of interest.

During the scanning process in this example, the measurement compartment was longitudinally moved longitudinally over the produce. On the surface of each area to be scanned, several areas of interest (AOI) locations were selected and marked. After the scanning, each bell pepper was taken to measure TSS by destructive tests. The pepper fruit was juiced and three to five drops of the juice were taken to determine TSS content with a digital refractometer (Atago, Japan). The TSS content was expressed in Brix%. Altogether 300 samples were taken and used in the ML training procedure. The test result of the ML model on 80 samples is depicted in FIG. 10, where the non-destructively predicted TSS content based on the hyperspectral imaging of each sample is shown in relation to the destructively measured TSS content. The ML model prediction error is 0.25 Brix%.

As seen from the FIG. 10, the herein disclosed hyperspectral imaging system provided a reliable prediction of actual TSS content.

Although some embodiments of the invention are not limited in this regard, discussions utilizing terms such as, for example, "processing," "computing." "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term set when used herein may include one or more items. Unless explicitly stated, the method embodiments described herein are not constrained to a particular order or sequence. Additionally, some of the described method embodiments or elements thereof can occur or be performed simultaneously, at the same point in time, or concurrently.

As used herein, the terms "approximately", "essentially" and "about" in reference to a number are generally taken to include numbers that fall within a range of 5% or in the range of 1% in either direction (greater than or less than) the number unless otherwise stated or otherwise evident from the context (except where such number would exceed 100% of a possible value). Where ranges are stated, the endpoints are included within the range unless otherwise stated or otherwise evident from the context.

As used herein, the singular forms "a," "an" and "the" include plural referents unless the context clearly dictates otherwise.

As used herein, "optional" or "optionally" means that the subsequently described event or circumstance does or does not occur, and that the description includes instances where said event or circumstance occurs and instances where it does not.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination or as suitable in any other described embodiment of the disclosure. No feature described in the context of an embodiment is to be considered an essential feature of that embodiment, unless explicitly specified as such.

Although stages of methods, according to some embodiments, may be described in a specific sequence, the methods of the disclosure may include some or all of the described stages carried out in a different order. In particular, it is to be understood that the order of stages and sub-stages of any of the described methods may be reordered unless the context clearly dictates otherwise, for example, when a latter stage requires as input an output of a former stage or when a latter stage requires a product of a former stage. A method of the disclosure may include a few of the stages described or all of the stages described. No particular stage in a disclosed method is to be considered an essential stage of that method, unless explicitly specified as such.

Although the disclosure is described in conjunction with specific embodiments thereof, it is evident that numerous alternatives, modifications, and variations that are apparent to those skilled in the art may exist. Accordingly, the disclosure embraces all such alternatives, modifications, and variations that fall within the scope of the appended claims. It is to be understood that the disclosure is not necessarily limited in its application to the details of construction and the arrangement of the components and/or methods set forth herein. Other embodiments may be practiced, and an embodiment may be carried out in various ways.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:

1. A system for imaging-based quality assessment of raw produce loads, the system comprising:

an imaging structure comprising a mounting beam, wherein the mounting beam comprises a measurement chamber comprising:

one or more light sources;

one or more optical sensors operating in visual and/or non-visual spectra, and one or more additional sensors;

wherein the measurement chamber is configured to minimize external light from reaching the one or more camera; and wherein the mounting beam is configured to allow vertical, lateral and/or longitudinal and movement of the measurement chamber, a processing unit comprising:

a memory; and a processor coupled to the memory programmed with executable instructions, the executable instructions comprising a monitoring component for:

a. controlling the vertical, lateral and/or longitudinal movement of the measurement chamber relative to the mounting beam, so as to position the measurement chamber at a predetermined position relative to produce in the produce load;

b. controlling one or more opto-mechanical parameters of the one or more optical sensors, the opto-mechanical parameters selected from: a field of view of the one or more optical sensors, exposure time, aperture, gain, sensitivity, frame rate and any combination thereof;

c. controlling a position, orientation, light projection and/or light intensity of the one or more light sources;

d. triggering signal acquisition by the one or more optical sensors and the one or more additional sensors, upon positioning and/or configuration of the imaging chamber, the one or more optical sensors and/or the one or more light sources;

e. receiving spectral data from the one or more optical sensors and sensor data from the one or more additional sensors;

f. fusing the spectral and sensor data;

g. feeding the fused data into an AI, ML, DL algorithm and/or big-data analytics model, to derive internal and/or external quality attributes of the produce; and h. producing a report indicating the derived internal and/or external quality attributes.

2. The system of claim 1, wherein the processor is further configured to identify movement of the container relative to the mounting beam and to time the signal acquisition to the identified movement.

3. The system of claim 1, wherein the one or more additional sensors is selected from a distance sensor, a lidar sensor, a depth sensor, a temperature sensor, an ultrasonic sensor, fluorescence sensor, X-ray sensor, XRF (X-ray fluorescence) sensor, MRI sensor, dielectric sensor, or any combination thereof.

4. The system of claim 1, wherein the monitoring component is configured to monitor and/or analyze environmental parameters selected from load velocity, light intensity, distance to object of interest, and any combination thereof.

5. The system of claim 1, wherein the monitoring component is configured to monitor and analyze a performance of the system to ensure stable and controlled system performance.

6. The system of claim 5, wherein the processor is further configured to adjust one or more system parameters, based on the monitored performance, wherein the one or more system parameters are selected from distance to object of interest, exposure time, aperture, frame rate, gain/sensitivity and any combination thereof.

7. The system of claim 1, wherein the processor is configured to monitor the produce load essentially in its entirety.

8. The system of claim 1, wherein the processor is configured to analyze selected samples of the produce in the produce load, wherein the samples are located at various area/parts of the produce load and wherein the analysis comprises extrapolating the sample data to the entire produce load.

9. The system of claim 1, wherein the extrapolating comprises applying statistical analyses.

10. The system of claim 1, wherein the one or more optical sensors comprise at least one hyperspectral camera.

11. The system of claim 1, wherein the one or more light sources comprise halogenic light sources.

12. The system of claim 1, wherein triggering the signal acquisition comprises controlling a timing of the signal acquisition.

13. The system of claim 1, wherein the monitoring component is further configured to calculate a spatial distribution of subsections of the produce with different internal/external attributes and or a degree of homogeneity of the produce in the load.

14. The system of claim 1, further comprising a sensor configured to sense positioning of a load underneath the mounting beam.

15. The system of claim 1, wherein the internal and/or external quality attributes are selected from chemical composition, biochemical composition, physical composition and/or biophysical composition, like dry matter, total soluble solids, sugar content, moisture, acidity, titratable acidity, pH, starch, ascorbic acid, external and/or internal defects, moldiness, decay, pigments, size, shape, texture, contaminants, and any combination thereof.

16. The system of claim 1, wherein the monitoring component is further configured to derive one or more complex parameters from the one or more of the internal and/or external quality attributes, wherein the one or more complex attribute comprise maturity, ripeness, shelf-life, storability and any combination thereof.

17. A method for assessing a quality of a produce load, the method comprising:

a. entering a load of raw produce into a monitoring station, b. positioning a measurement chamber at a predetermined position relative to the produce, wherein the measurement chamber comprises one or more light sources, one or more optical sensors and one or more additional sensors, c. capturing images and collecting data of the produce and retrieving spectral, hyperspectral, image and sensory data therefrom; and d. fusing the retrieved data;

e. feeding the fused data into an AI, ML, DL algorithm and/or big-data analytics model to derive internal and/or external quality attributes of the produce; and f. producing a report indicating the internal and/or external quality attributes of the produce, as assed.

18. The method of claim 17, wherein the one or more internal and/or external parameters are selected from chemical composition, biochemical composition, physical composition and biophysical composition, like dry matter, total soluble solids, sugar content, moisture, acidity, titratable acidity, pH, starch, ascorbic acid, external and/or internal defects, moldiness, decay, pigments, size, shape, texture, contaminants, and any combination thereof and/or one or more of the internal and/or external quality attributes, wherein the one or more complex attribute comprise maturity, ripeness, shelf-life, storability and any combination thereof.

19. The method of claim 17, further comprising moving the measurement chamber, to thereby allow scanning of different areas of the produce and determining a spatial distribution and/or degree of homogeneity of the produce load.

20. The method of claim 17, further comprising detecting, using a sensor, a change in the position of the produce load relative to the measurement chamber and automatically triggering signal acquisition by the one or more optical sensors and the one or more additional sensors.

* * * * *